US008076504B2

(12) United States Patent
Kubatova et al.

(10) Patent No.: US 8,076,504 B2
(45) Date of Patent: Dec. 13, 2011

(54) METHOD FOR PRODUCTION OF SHORT CHAIN CARBOXYLIC ACIDS AND ESTERS FROM BIOMASS AND PRODUCT OF SAME

(75) Inventors: Alena Kubatova, Grand Forks, ND (US); Wayne S. Seames, Grand Forks, ND (US); Brian M. Tande, Fargo, ND (US)

(73) Assignee: The University of North Dakota, Grand Forks, ND (US)

( * ) Notice: Subject to any disclaimer, the term of this patent is extended or adjusted under 35 U.S.C. 154(b) by 415 days.

(21) Appl. No.: 12/319,028

(22) Filed: Dec. 31, 2008

(65) Prior Publication Data

US 2009/0182166 A1 Jul. 16, 2009

Related U.S. Application Data

(60) Provisional application No. 61/009,663, filed on Dec. 31, 2007.

(51) Int. Cl.
*C07C 69/66* (2006.01)
*C07C 69/52* (2006.01)
*C07C 51/00* (2006.01)
*C07B 53/00* (2006.01)

(52) U.S. Cl. ......... 560/179; 560/205; 562/599; 562/606

(58) Field of Classification Search ........................ None
See application file for complete search history.

(56) References Cited

U.S. PATENT DOCUMENTS

| | | | |
|---|---|---|---|
| 4,364,745 A | 12/1982 | Weil | |
| 4,992,605 A | 2/1991 | Craig et al. | |
| 5,233,109 A | 8/1993 | Chow | |
| 5,520,708 A | 5/1996 | Johnson et al. | |
| 5,578,090 A | 11/1996 | Bradin | |
| 5,705,722 A | 1/1998 | Monnier et al. | |
| 5,899,339 A * | 5/1999 | Noda | 209/155 |
| 5,986,133 A | 11/1999 | Holtzapple et al. | |
| 6,284,008 B1 | 9/2001 | Caprotti | |
| 6,844,447 B2 * | 1/2005 | Zhong et al. | 548/543 |
| 7,014,668 B2 | 3/2006 | Golubkov et al. | |
| 7,041,738 B2 | 5/2006 | Krull et al. | |
| 7,045,100 B2 | 5/2006 | Ergun et al. | |
| 2003/0093942 A1 | 5/2003 | Jordan | |
| 2003/0167681 A1 | 9/2003 | Delgado Puche | |
| 2004/0074760 A1 | 4/2004 | Portnoff et al. | |
| 2004/0231236 A1 | 11/2004 | May et al. | |
| 2005/0232956 A1 | 10/2005 | Bist et al. | |
| 2006/0024801 A1 | 2/2006 | Holtzapple et al. | |
| 2006/0236598 A1 | 10/2006 | Selvidge | |
| 2007/0014895 A1 | 1/2007 | Holtzapple et al. | |
| 2007/0039240 A1 | 2/2007 | Carroway | |
| 2007/0068848 A1 | 3/2007 | Monnier et al. | |
| 2007/0137097 A1 | 6/2007 | Ikura | |
| 2007/0144060 A1 | 6/2007 | Ikura | |
| 2007/0170091 A1 | 7/2007 | Monnier et al. | |

OTHER PUBLICATIONS

Maher et al, Bioresource Technology, Pyrolysis of Triglyceride Materials for the Production of Renewable Fuels and Chemicals, 2007, 98, pp. 2351-2368.*
R. O. Dunn, et al., "Low-Temperature Properties of Triglyceride-Based Diesel Fuels: Transesterified Methyl Esters and Petroleum Middle Distillate/Ester Blends", from JAOCS, vol. 72, No. 8, pp. 895-904 (1995).
I. Lee, et al. "Use of Branched-Chain Esters to Reduce the Crystallization Temperature of Biodiesel", from JAOCS, vol. 72, No. 10, pp. 1155-1160 (1995).
S. P. R. Katikaneni, et al., "Catalytic Conversion of Canola Oil to Fuels and Chemicals Over Various Cracking Catalysts", from The Canadian Journal of Chemical Engineering, vol. 73, pp. 484-497 (1995).
M. S. Graboski, et al., "Combustion of Fat and Vegetable Oil Derived Fuels in Diesel Engines," from Prog. Energy Combust. Sci., vol. 24, pp. 125-164 (1998).
F. Ma, et al., "Biodiesel Production: A Review", from Bioresource Technology 70, pp. 1-15 (1999).
R. O. Dunn, "Alternative Jet Fuels From Vegetable Oils", from American Society of Agricultural Engineers, vol. 44, pp. 1751-1757 (2001).
Y. S. Ooi, et al., "Catalytic Conversion of Palm Oil-Based Fatty Acid Mixture to Liquid Fuel", from Biomass and Bioenergy 27, pp. 477-484 (2004).
E. Corporan, et al., "Impacts of Biodiesel on Pollutant Emissions of a JP-8-Fueled Turbine Engine", from Journal of the Air & Waste Management Assoc., vol. 55, pp. 940-949 (Jul. 2005).
S. M. Sadrameli, et al., "Systematics of Renewable Olefins From Thermal Cracking of Canola Oil," from J. Anal. Appl. Pyrolysis 78, pp. 445-451 (2007).
B. K. Bhaskara Rao, "Modern Petroleum Refining Processes", Oxford & IBH Publishing Co. Pvt. Ltd. (5th Ed. 2007) pp. 304-407.
Official Search Report and Written Opinion of the international Searching Authority in counterpart foreign Application No. PCT/US 08/14145 filed Dec. 31, 2008.

* cited by examiner

*Primary Examiner* — Paul A Zucker
(74) *Attorney, Agent, or Firm* — Kinney & Lange, P.A.

(57) ABSTRACT

A method for producing a mixture of short chain carboxylic acids from biomass includes adding biomass to a reactor vessel, heating the biomass to crack it, removing undesired and unreacted materials and light ends from the cracked biomass, and removing a mixture containing carboxylic acids having carbon chain lengths between C2 and C16. A composition includes a carboxyl group-containing compound derived by cracking biomass and having a carboxyl carbon chain length between C2 and C16.

22 Claims, 5 Drawing Sheets

US 8,076,504 B2

METHOD FOR PRODUCTION OF SHORT CHAIN CARBOXYLIC ACIDS AND ESTERS FROM BIOMASS AND PRODUCT OF SAME

CROSS-REFERENCE TO RELATED APPLICATION(S)

This application claims the benefit of U.S. Provisional Application No. 61/009,663 filed on Dec. 31, 2007, for "Method to Produce Short Chain Carboxylic Acids and Esters from Biomass" by A. Kubatova and W. Seames, and U.S. Provisional Application No. 61/074,206 filed on Jun. 20, 2008, for "Thermal Cracking Method to Produce Short Chain Carboxylic Acids from Biomass" by A. Kubatova and W. Seames, which are incorporated by reference.

STATEMENT OF GOVERNMENT INTEREST

This invention was made, at least in part, with U.S. Government support under contract numbers 04-C-GA-ERAU, amendment #039, awarded by the Federal Aviation Administration. The U.S. Government may have certain rights in this invention

BACKGROUND

One of the key challenges facing modern industrialized society is the rapid depletion of crude oil, which is the primary source for most transportation fuels and many organic chemicals. The petrochemical industry represents a substantial benefit to human society and the invention and commercialization of alternative sources for petrochemicals is of great importance.

Two categories of organic chemicals that are often produced from petroleum are short chain carboxylic acids and short chain carboxylic esters. These chemicals have a wide range of uses, which include serving as monomers for many types of polymers, paints, coatings, and fragrance sources for perfumes and other commodities.

The use of short chain carboxylic acids as monomers is of particular importance. Substantial efforts have been made in recent years to develop usable polymers from fatty acids bound within triacylglycerides. Processes such as the Soyol process incorporate triacylglyceride fatty acids directly into polymers. One disadvantage of these processes is that the resulting polymers have properties that are different, and in many cases inferior, to existing polymers produced from petrochemical-based monomers.

Surprisingly, very little work has been done to chemically modify triacylglycerides to produce more useful fatty acid-based monomers and other commodity chemicals that are identical, or nearly identical, to existing monomers. Thus, a need exists to provide an alternative source for these chemicals so that demand can be satisfied as the source material, crude oil, diminishes.

SUMMARY

The invention described herein provides a process for the production of commercial grade short chain carboxylic acids and short chain carboxylic esters from triacylglycerides, long chain fatty acids, long chain lipids, or similar chemicals.

One embodiment of the present invention is a method for producing a mixture of short chain carboxylic acids from biomass. The method includes adding biomass to a reactor vessel, heating the biomass to crack it, removing undesired and unreacted materials and light ends from the cracked biomass, and removing a mixture containing carboxylic acids having carbon chain lengths between C2 and C16.

Another embodiment of the present invention is a composition including a carboxyl group-containing compound derived by cracking biomass and having a carboxyl carbon chain length between C2 and C16.

In a first aspect of the invention, an oil containing primarily fatty acids embedded within triacylglyceride obtained from plants, expressed from algae, derived from animal biomass, or derived from other sources is added to a reactor vessel.

In a second aspect of the invention, the oil is heated in the reactor vessel to a temperature from about 100° C. to about 600° C. at a pressure ranging from about vacuum conditions to about 3000 psia for a time sufficient to crack the oil. During the process, undesired material, unreacted oil, and light ends are removed from the cracked oil. The purified material contains chemical compounds that are desirable for isolation as short chain carboxylic acids and fuels.

In a third aspect of the invention, short chain carboxylic acid compounds are extracted from fuel compounds and are purified. The short chain carboxylic acids generally include fatty acids with 2-12 carbon atoms (C2-C12). Desirable fuel components generally include C4-C16 alkanes, alkenes, aromatics, cycloparaffins, and alcohols.

In a fourth aspect of the invention, preferential extraction of selected fatty acids is carried out by liquid-liquid extraction using a basic aqueous solvent such as an amine like trimethylamine. The fatty acid rich solvent is regenerated to liberate the fatty acids from the solvent. Individual C2-C12 fatty acids are obtained in purified form by physical and/or chemical separation.

In a fifth aspect of the invention, preferential extraction of selected fatty acids is carried out by a sequential liquid-liquid extraction method whereby room temperature water is used to preferentially extract C2-C5 fatty acids, then higher temperature water or a basic aqueous solution is used to selectively extract C4-C7 fatty acids, and finally pressurized hot water or another solvent is used to preferentially extract C6-C12 fatty acids. After extraction individual C2-C12 fatty acids are obtained in purified form by physical and/or chemical separation.

In a sixth aspect of the invention, esterification of one or more of the individual C2-C12 short chain fatty acids or a mixture thereof using an alcohol or a mixture of alcohols is carried out. Esterification alcohols employed for the esterification include, but are not limited to, methanol, ethanol, normal propanol, iso-propanol, normal butanol, iso-butanol, allyl alcohol, and other alcohols. After esterification, the esterified material is separated from unreacted material.

DETAILED DESCRIPTION

Figure 1:
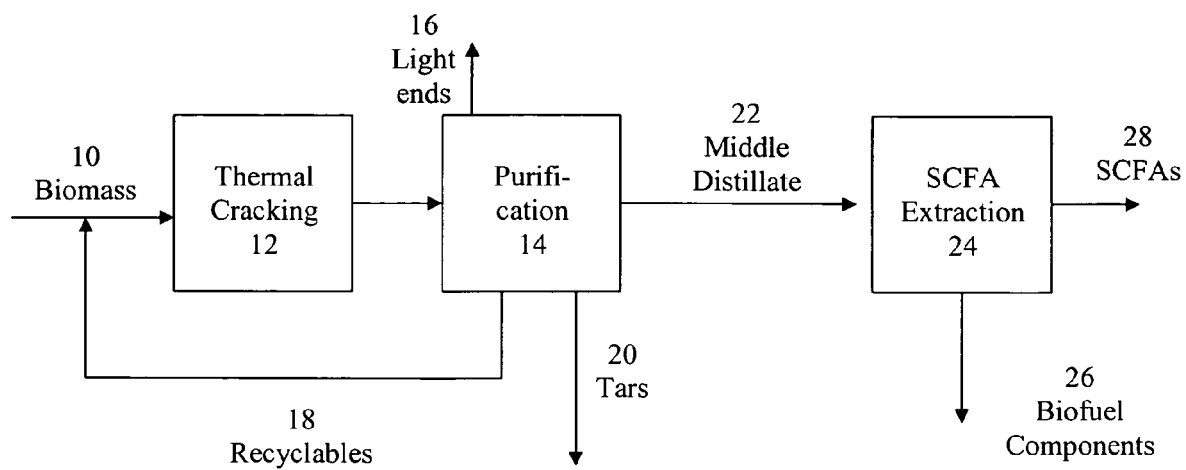
FIG. 1 is a simplified block diagram illustrating one embodiment of a short chain carboxylic acid production process.

In order to accurately describe the invention, the following terms are defined to have the following associated meanings:

"Biofuel" means any fuel that is derived from plant or animal biomass.

"Biomass" means any organic, non-fossil material that is derived from the mass of any biological organism excluding mass that has been transformed by geological processes in substances such as coal or petroleum.

"Biomass oil" means any oil derived from a biomass source.

"Carboxyl group" means a portion of a chemical molecule that contains a carbon atom with a double bond connection to an oxygen atom and where the same carbon atom is also connected to a hydroxyl group, and where no other atoms are connected by a chemical bond to the doubly-bonded oxygen atom. This structure is acidic because in certain solutions, the hydrogen atom on the hydroxyl group readily dissociates from the chemical molecule, forming a cation (the hydrogen atom) and an anion (the remainder of the chemical molecule).

"Catalyst" means those substances that accelerate the rate or ease of a chemical reaction.

"Catalytic cracking" means a cracking process that uses a catalyst.

"Cracking" means any process that changes the chemical composition of an organic chemical or chemical mixture by cleaving one or more carbon-carbon bonds in one or more molecules.

"Crop" means any plant.

"Diesel" means a fuel made commercially for diesel-powered vehicles.

"Carboxylic acid ester" is a chemical compound formed by the reaction of a carboxylic acid and an alcohol, where a terminal hydrogen atom of the carboxyl group is replaced by a carbon chain (radical) from the alcohol.

"Fatty acid" means a carboxylic acid with a saturated or unsaturated aliphatic tail.

"Hydroxyl group" means a portion of a chemical molecule containing an oxygen atom connected by a single bond to a hydrogen atom and also connected by a single bond to the rest of the chemical molecule, where the hydrogen atom is not connected to any other atoms.

"Light ends" means chemicals which stay in the gaseous phase at conditions of temperature and pressure at which middle distillates are in the liquid phase.

"Middle distillate" means a chemical which has properties amenable for inclusion in a gasoline, kerosene, or diesel type fuel or which have a volatility similar to those paraffins and/or olefins which are amenable for inclusion in a gasoline, kerosene, or diesel type fuel. A middle distillate can also contain carboxylic acids.

"Plant" means any living organism that is a member of the kingdom Plantae or of the division Chiorphyta (green algae).

"Plant oil" means lipids that are derived from plant sources. Examples of plant oil include crop oils or oilseeds and vegetable oils.

"Short chain carboxylic acid" means a chemical compound with no more than 12 carbons that contains a carboxyl group.

"Short chain carboxylic ester" means a chemical compound derived from a short chain carboxylic acid in which the carboxylic acid group is replaced by an ester group.

"Tars" are very long chain chemical compounds generated during the cracking reaction.

"Thermal cracking" means a cracking process that involves the addition of energy in the form of thermal energy as measured by an increase in the temperature of the substance being cracked.

"Triacylglyceride" or "TG" is a major component of unmodified plant oils, it is an ester of glycerol and three fatty acids.

"Unreacted raw material" is the material in the cracking reactor product stream that has a chemical composition that is not amenable as a middle distillate blend component and can be further exposed to cracking reactor conditions and transformed into middle distillate and/or light ends and/or tars. These compounds may be chemically identical to the original starting material, a fatty acid whose length is identical or similar to the fatty acid chains on an original triacylglyceride (when triacylglycerides are in the feedstock) or a partially cracked paraffin, olefin, or carboxylic acid that has too many carbon atoms in the primary carbon chain to be amenable as a middle distillate blend component.

No previous invention or published work has been identified that describes the use of thermal and catalytic cracking for the formation of short chain carboxylic acids and/or esters. Thus, there is a need to develop a method that allows a crop oil, biologically generated lipid, or animal fat oil feedstock to be converted into these important and valuable chemicals. The current invention utilizes separation technologies coupled with thermal/catalytic cracking techniques in order to develop crop oil-, biologically generated lipid-, or animal fat-based chemicals that can replace commercially available chemicals generated from other feed stock sources.

The present invention is directed to the production and purification of C2 to C16 short chain carboxylic acids with potentially subsequent conversion to short chain carboxylic esters from plant oils, biologically generated lipids, or animal fats. Specifically, the feedstocks are triacylglyceride compounds. This invention provides a means to produce these valuable and necessary chemicals from new feedstocks, not currently utilized in their production. The chemical modifications, based on the use of cracking and separation techniques, are designed to produce commercial-quality short chain carboxylic acid chemical products that can directly replace comparable chemical products generated from other feedstock sources.

Research exploring triacylglycerides thermal and catalytic cracking (individual triacylglycerides and vegetable oils) has occurred sporadically in the last few decades. From these works, a set of organic reactions have been identified as occurring during the thermal/catalytic cracking of triacylglycerides. These reactions are illustrated in Table 1 below.

TABLE 1

1. Thermolysis of the TG ester bond

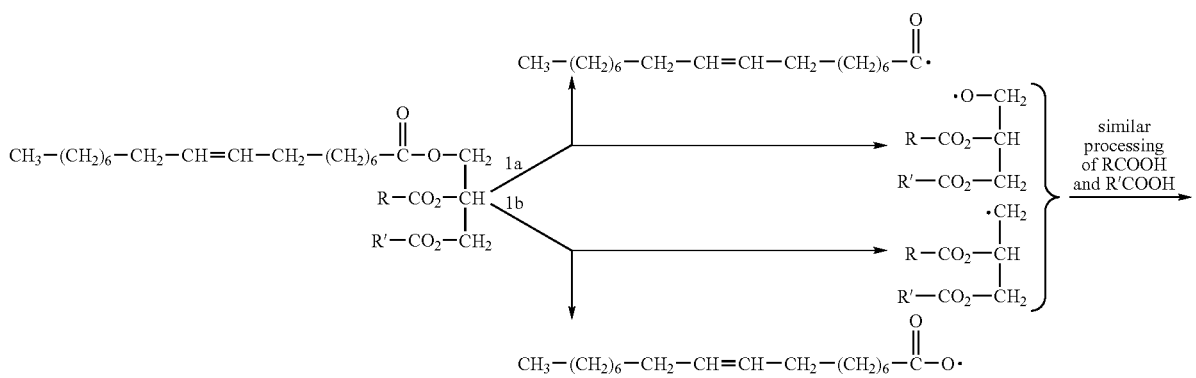

2. Deketenization (continuation of reaction 1a)

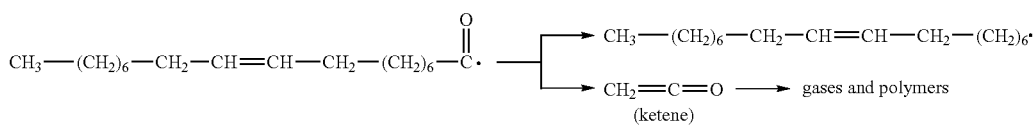

3. Decarboxylation (continuation of reaction 1a)

4. Stabilization of radicals

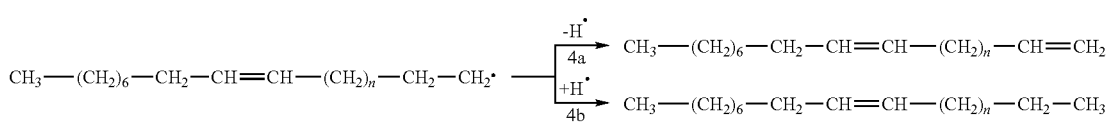

5. Cracking of unsaturated hydrocarbons (shown for the predominant allyl position)

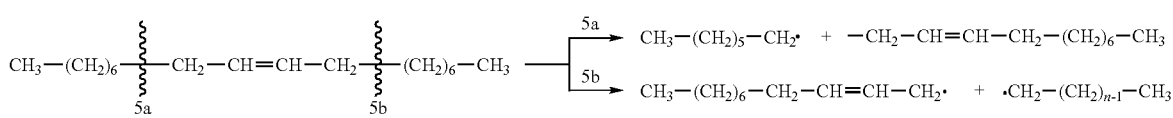

6. Isomerization
6a. Moving the double bond
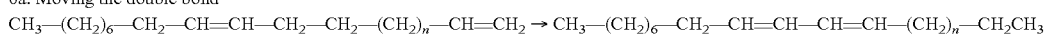
6b. Forming more stable radicals
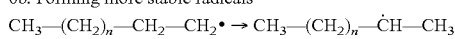
7. Formation of branched radicals
7a. Direct isomerization to form more stable radicals

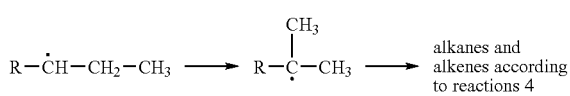

7b. Reactions of radicals with double bonds

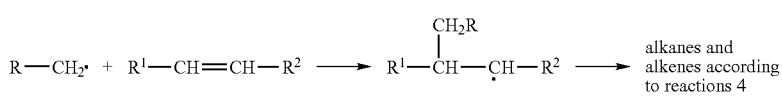

8. Diels-Alder reaction

TABLE 1-continued

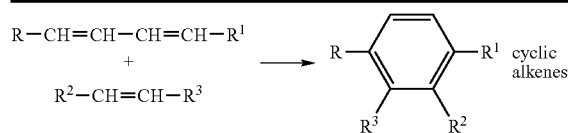

9. Dehydrogenation and hydrogenation

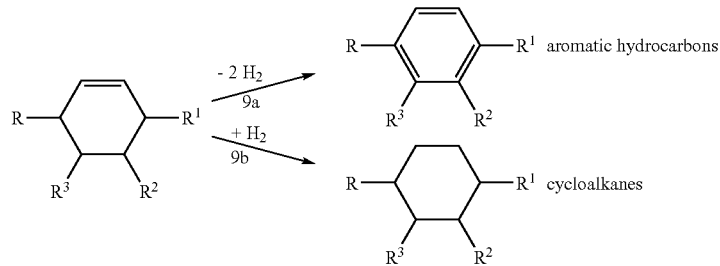

10. Termination
R—CH$_2$• + R$^1$CH$_2$• → R—CH$_2$—CH$_2$—R$^1$
Previously unknown or uncommon reactions
11. Fatty acid cracking

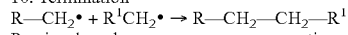

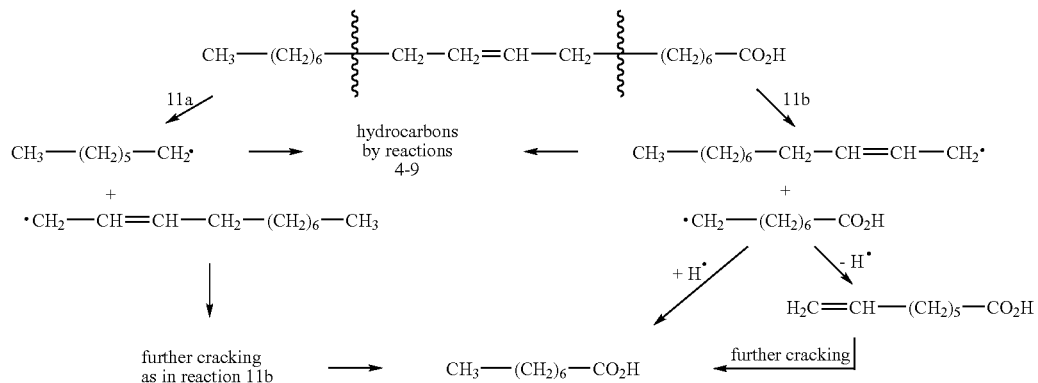

The chemical composition of crackate generated, typically obtained from fresh or used vegetable oil, was reported in a number of studies. The known overall process routes are diagramed below in Table 2.

TABLE 2

| | Cracking conditions | | |
|---|---|---|---|
| Products | Route 1[a] (piqui oil) 300° C. catalyzed % (w/w) | Route 2[b] (canola oil) 450° C. catalyzed % (w/w) | Route 3[c] (safflower oil, high in oleic acid) 300-360° C. non-catalyzed % (w/w) |
| Alkanes C$_3$-C$_5$ | 0 | | |
| Alkanes C$_6$-C$_{10}$ | 14.2 | | Some (C$_6$-C$_9$) |
| Alkanes C$_{11}$-C$_{16}$ | 25.3 | | Most (C$_{15}$-C$_{18}$) |
| Alkanes C$_{17}$-C$_{24}$ | 2.4 | | |
| Total linear alkanes | 41.9 | | Most |
| Total branched alkanes | 2.6 | | |
| Total identified alkanes | 44.5 | | 37.5 |
| Olefins C$_5$-C$_{10}$ | 12.0 | | |
| Olefins C$_{11}$-C$_{16}$ | 14.3 | | |
| Olefins C$_{17}$-C$_{20}$ | 0 | | |
| Dienes | 0 | | 8.1 |

TABLE 2-continued

| | Cracking conditions | | |
|---|---|---|---|
| Products | Route 1[a] (piqui oil) 300° C. catalyzed % (w/w) | Route 2[b] (canola oil) 450° C. catalyzed % (w/w) | Route 3[c] (safflower oil, high in oleic acid) 300-360° C. non-catalyzed % (w/w) |
| Total linear olefins | 26.3 | | Most |
| Total branched olefins | 1.3 | | |
| Total identified olefins | 27.6 | | 22* |
| Total identified aliphatic hydrocarbons | 72.1 | 7.2 | >57.5* |
| Total BTEX | 0 | 28.1 | Abundant |
| Other identified aromatics | 0 | 10.3 | |
| Total identified aromatics | 0 | 38.4 | 2.2 |
| Furanes and ketones | | 8.8 | |
| Alcohols and ketones | | 5.8 | |
| Fatty acids C$_2$-C$_3$ | 0 | | Traces |
| Fatty acids C$_4$-C$_9$ | 0 | | Some (C$_7$-C$_9$) |
| Fatty acids C$_{10}$-C$_{11}$ | 0 | | Traces except for C10 |
| Fatty acids C$_{16}$ | 0 | | Most (TG acids) |
| Total identified fatty acids | 0 | | 11.5 |

TABLE 2-continued

| | Cracking conditions | | |
|---|---|---|---|
| Products | Route 1[a] (piqui oil) 300° C. catalyzed % (w/w) | Route 2[b] (canola oil) 450° C. catalyzed % (w/w) | Route 3[c] (safflower oil, high in oleic acid) 300-360° C. non-catalyzed % (w/w) |
| Acids (unspecified) and esters | | | 2.2 |
| Total | 72.1 | 62.9 | 81.4 |

Where
[a]Route 1 is catalytic cracking at low temperature: Alencar, 1983; at 300° C.;
[b]Route 2 is catalytic cracking at high temperature: Katikaneni, 1995; at 450° C.;
[c]Route 3 is non-catalytic cracking at low temperature: Schwab, 1988; at 300-360° C.;
*An additional 9.7-10.1% is listed as "unresolved unsaturates."

Surprisingly, conditions were discovered that allow the generation of commercially-viable concentrations of short chain carboxylic acids. When purified to remove light ends, heavy ends, and unreacted material, the resulting middle distillate contains 5% or more short chain carboxylic acids, preferably 20% or more short chain carboxylic acids, more preferably 30% or more short chain carboxylic acids, and most preferably 60% or more short chain carboxylic acids. The present invention uses thermal or catalytic cracking technologies known in the art coupled with separation technologies such as distillation, filtration, solvent extraction, and related technologies, for the specific purpose of producing commercial quality short chain carboxylic acids from biomass. Previously, these same short chain carboxylic acids were produced from sources other than biomass.

It has been further discovered that there is an economic advantage to further process some or all of the purified short chain carboxylic acids or a mixture thereof in order to produce short chain carboxylic acid esters. This aspect of the invention uses esterification reactions with one or more alcohols, these reactions being known in the art, coupled with separation technologies such as distillation, filtration, solvent extraction, and related technologies, for the specific purpose of producing commercial quality short chain carboxylic acid esters that are derived from biomass. The short chain carboxylic acid esters that can be produced by this process range from 2 to 16 carbon atoms in length.

The raw material for this new process is any triacylglyceride, free fatty acid or other carboxylic acid representing a group of chemical compounds that can be found in plants or plant oils or medium (C10-C14) and longer (greater than C16) chain fatty acids that are naturally synthesized and found in biomass such as algae, animal fats, or modified materials. The triacylglycerides in plant oils generally contain three medium (C10-C14) and/or long (greater than C16) chain fatty (naturally synthesized carboxylic) acids connected via a glycerol group. These medium and/or long chain fatty acids, can be purified, separated, and chemically modified for use as a food source or chemical feedstock or as a potential transportation fuel. Plants and plant oils include, but are not limited to, flax, soybean, safflower, sunflower, sesame, canola, rapeseed, jatropha, primrose, poppy, camelina, crambe, olive, coconut, palm, cotton, corn, soybean, jojoba, pennycress, tomato and nuts. Compositions of some major commercially-available crop oils are listed in Table 3.

TABLE 3

| Crop | | Polyunsaturated % | | | Mono % | Saturated % | | |
|---|---|---|---|---|---|---|---|---|
| Name | Lipid % | 18:3 | 18.2 | 22:1 | 18:1 | 18:0 | 16:0 | Total |
| Corn | 4 | — | 59 | — | 24 | 17 | — | 17 |
| Crambe | 26-38 | 5 | 9 | 55-60 | 17 | — | — | 3 |
| Flax | 35 | 58 | 14 | — | 19 | 4 | 5 | 9 |
| Soybean | 20 | 7 | 50 | — | 26 | 3 | 12 | 15 |
| Mid-Oleic Soybean | 20 | 0.5 | 28 | — | 60 | 4 | 9 | 13 |
| Safflower | 59 | — | 75 | — | 13 | 12 | — | 12 |
| Sunflower | 47 | — | 74 | — | 23 | 3-4 | 7 | 10-11 |
| NuSun Sunflower | 45-50 | — | 15-35 | — | 50-75 | 3-4 | 4-5 | 7-9 |
| High Oleic Sunflower | 45-50 | — | 7 | — | 83 | 4 | 5 | 9 |
| Primrose | 17 | — | 81 | — | 11 | 2 | 6 | 8 |
| Sesame | 49.1 | — | 45 | — | 42 | 13 | — | 13 |
| Canola | 30-35 | 8 | 22 | 1 | 64 | 3 | 1 | 4 |
| Rapeseed | 30-35 | 8 | 22 | 30-45 | 19 | 4 | 1 | 5 |
| Olive | 20 | — | 8 | — | 75 | 16 | — | 16 |
| Coconut | 35 | — | 3 | — | 6 | — | 91 | 91 |
| Palm | 35 | — | 2 | — | 13 | — | 85 | 85 |
| Camelina | 31 | 31.2 | 23.1 | 2.8 | 16.8 | 3.0 | 7.8 | 10.8 |

Typical fatty acids contained in crop oils include saturated and unsaturated fatty acids. Saturated fatty acids do not contain any double bonds or other functional groups. Unsaturated fatty acids contain two or more carbon atoms having a carbon-carbon double bond. Saturated acids include stearic (C18; 18:0), palmitic (C16; 16:0), myristic (C14; 14:0), and lauric (C12; 12:0). Unsaturated acids include those such as linolenic (cis, cis, cis C18; 18:3), linoleic (cis, cis C18; 18:2), oleic (cis C18; 18:1), hexadecanoic (cis, cis C16; 16:2), palmitoleic (cis C16; 16:1), and myristoleic (cis C14; 14:1).

It is known that thermal and catalytic cracking of medium (C10-C14) and/or long (greater than C16) chain fatty (naturally synthesized carboxylic) acids, coupled with separation and purification technologies, can produce a mixture of chemicals suitable for use as a fuel or a fuel blendstock, most specifically as components in diesel, kerosene, aviation turbine, and motor gasoline fuels. An example of a method for deriving fuel from biomass is described in U.S. patent application Ser. No. 11/824,644 (Seames), which is herein incorporated by reference. U.S. patent application Ser. No. 11/824,644 describes a process for producing a fuel from biomass with a cloud point below −10° C. The present invention describes a process that can produce short chain carboxylic acids and carboxylic acid esters while also producing materials suitable for use fuels or fuel blendstocks. Combining production of short chain carboxylic acids and acid esters with fuel or fuel products offers the ability to produce not one but two beneficial products using one set of cracking parameters.

In the cracking process, energy is used to break carbon-carbon bonds. Once broken, each carbon atom ends up with a single electron and free radicals. Reactions of the free radicals can lead to the various products illustrated in Table 1. The breaking of large organic molecules into smaller, and more useful, molecules can be achieved by using high pressures and/or temperatures with a catalyst (catalytic cracking) or without (thermal cracking). Previous research has shown that medium (C10-C14) and long (greater than C16) chain fatty (naturally synthesized carboxylic) acids are compatible for the cracking processes, using either thermal or catalytic cracking. These techniques have been used in previous inventions and studies to modify the chemical composition of crop oils or biodiesel. However, they have not been used to produce commercial quality short chain carboxylic acids and/or esters.

FIG. 1 is a simplified block flow diagram of one embodiment of the short chain carboxylic acid production process. Biomass (including crop oils, lipids and animal fat feedstocks) 10 is produced by processes now available or that may be discovered in the future. Biomass 10 may be preheated or directly fed into a cracking reactor for thermal cracking step 12. By varying the time, temperature, and pressure under which a particular feedstock remains under cracking conditions, the desired degree of cracking (conversion) can be controlled. Temperature and time (residence time) are the more important process variables with pressure playing a secondary role. The products of the cracking process are dependent upon the conditions of cracking and the original composition of biomass 10 and the gaseous environment present in the cracking reactor. Generally, biomass 10 is heated to a temperature ranging from 100° C. to 600° C. at pressures ranging from vacuum conditions to 3000 psia in the cracking reactor for residence times ranging from one to 180 minutes. The temperature range is more preferably 300° C. to 500° C. and most preferably 390° C. to 440° C. The cracking conditions are varied based on detailed chemical analyses in order to produce the optimal mixture of short chain carboxylic acids and fuel components.

A catalyst can be used to improve the yield of desirable products, decrease the formation of unwanted products, or increase the efficiency of the cracking reaction due to lower pressure, temperature, or residence time requirements. Catalysts include but are not limited to zeolites, carbon and rare metals such as palladium, niobium, molybdenum, platinum, titanium, aluminum, cobalt, gold and mixtures thereof.

The cracking output is subjected to a variety of processing and purification steps 14 dependent upon the material generated. The output from the cracking reactor depends upon the specific reactor design employed. The following are examples of reactor types known to those skilled in the art: batch, continuous flow through, flow through packed bed, and fluidized bed. Material generated in the cracking reactor can generally be defined as light ends 16, unreacted raw materials (recyclables) 18, residual materials or residue (tars) 20, and middle distillate 22.

Light ends 16 are unreacted vapor-phase materials that were added to the reactor to manipulate the cracking reaction, such as hydrogen, nitrogen, or water vapor, in addition to small molecular weight organic chemicals and hydrocarbons generated in the cracking reactor. The small molecular weight organic chemicals and hydrocarbons, such as methane, methanol, ethane, ethanol, n-pentane, i-pentane, pentene, pentanol n-butane, i-butane, butanol, butane, methyl ester, ethyl ester, etc., have chemical and physical properties that are undesirable (such as being too volatile) when present in substantial concentrations of short chain carboxylic acid extracts or middle distillate fuel components. Light ends are separated from the other material that exits the reactor by gas-liquid phase separation, distillation, condensation, or other processes in purification step 14.

Unreacted raw materials 18 are chemicals that enter the cracking reactor but are not converted to chemical compounds with carbon chains shorter than C16. These materials have some chemical and physical properties that are undesirable in the fuel products. Unreacted raw materials are separated from the middle distillate components by distillation or other separation techniques in purification step 14. Unreacted or uncracked raw materials 18 can then be returned to the cracking reactor, fed to a second cracking reactor or utilized for some other purpose.

Residual material or residue tars 20 are chemicals produced during cracking reactions that have a higher molecular weight, lower volatility and/or lower heating value than is desirable in middle distillate 22. Some of the residual components 20 can be separated from middle distillate 22 along with unreacted raw materials 18 and processed with these unreacted raw materials 18. Other residue components 20, typically those of higher molecular weight, will be in the form of solid material (at room temperature) after the cracking reaction. These compounds are typically known as "tars." Tars 20 may contain valuable chemical compounds, such as boiler fuel or other by-products that can be extracted from residual material 20 by various process methods including solvent extraction, distillation, etc or may contain chemicals that can be transformed by chemical reactions into valuable chemical compounds. Depending upon the design of the cracking reactor, tars 20 may not be amenable to further processing. Such tars 20 may be oxidized, combusted or otherwise removed from the cracking reactor or cracking catalysts by methods known in the art.

Middle distillate components 22 are short chain carboxylic acid compounds generated in the cracking reactor as well as those portions of the remaining material that contribute to desirable chemical and physical properties of fuel or fuel blend stock products.

Figure 2:
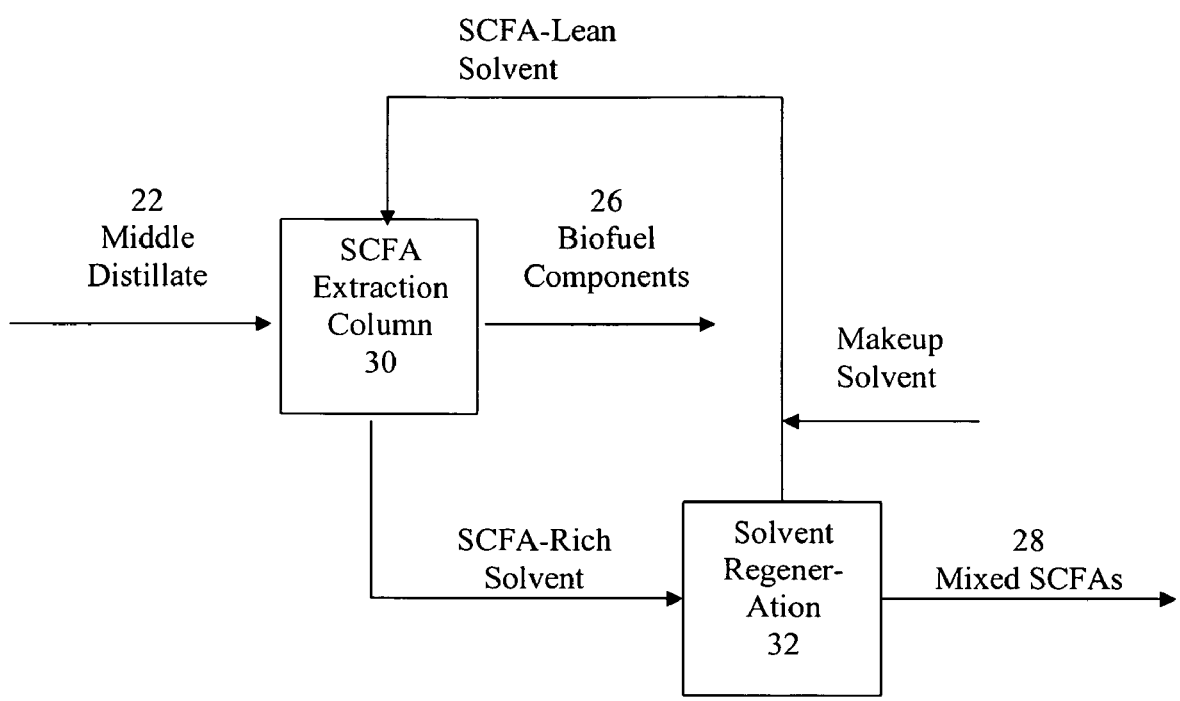
FIG. 2 is a simplified block diagram illustrating one embodiment of a short chain carboxylic acid extraction process.

Short chain carboxylic acids 28 are removed from middle distillate 22 using one or more process methods (step 24) including solvent extraction, distillation, etc. One embodiment of such a process is illustrated in FIG. 2. Middle distillate 22 enters a short chain fatty acid (SCFA) extraction column in step 30. Solvent, such as a 40% aqueous solution of trimethylamine, hot water or aqueous NaOH, is delivered to the extraction column. The solvent absorbs short chain fatty acids as it passes through the column, generating an SCFA-rich solvent while other components (e.g., biofuel components 26) remain in a separate liquid phase and are removed from the column separately. Mixed short chain fatty acids 28 are separated from the solvent. The solvent can then be regenerated (step 32) and delivered back to the extraction column.

Figure 3:
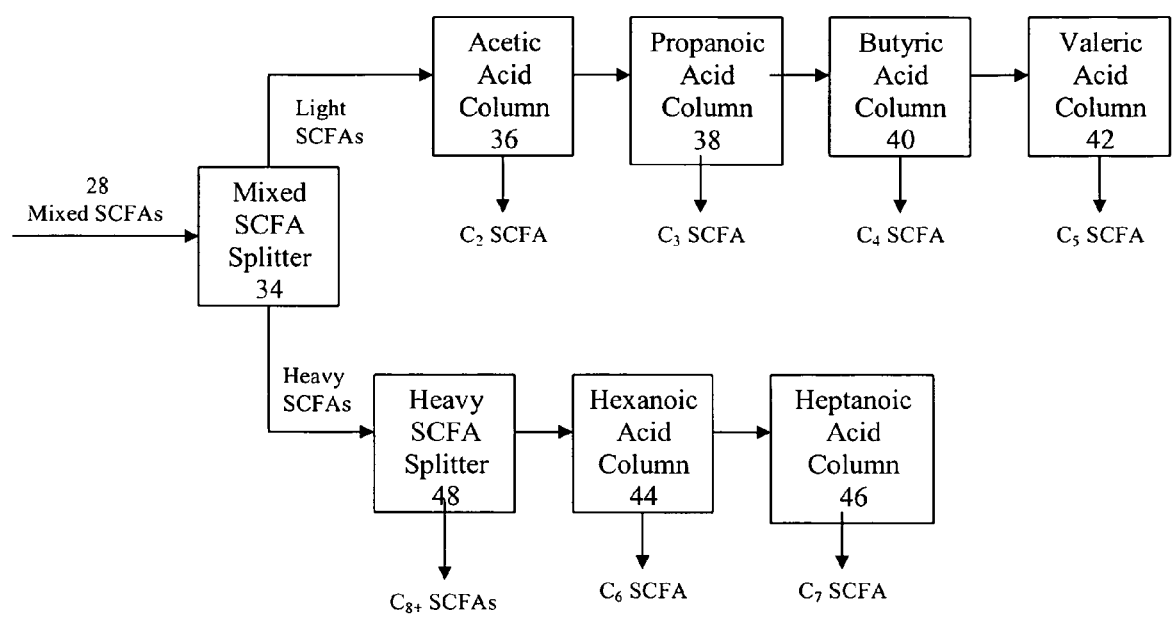
FIG. 3 is a simplified block diagram illustrating one embodiment of a short chain carboxylic acid purification process.

Once short chain carboxylic (fatty) acids 28 are isolated from middle distillate 22, they can be processed and purified further. Additional purification steps produce product streams that contain primarily single components or specific groups of short chain carboxylic acids 28. One embodiment of a typical purification scheme is shown in FIG. 3. Light fatty acids (C5 and shorter) and heavy fatty acids (C6 to C16) are separated from mixed short chain fatty acids 28 by mixed SCFA splitter 34. The separated fatty acids are then further separated using distillation columns to extract fatty acids of particular carbon chain lengths. For example, the light short chain fatty acids are delivered to a series of distillation columns. Acetic acid is isolated in acetic acid column 36, propanoic acid is isolated in propanoic acid column 38, butyric acid is isolated in butyric acid column 40 and valeric acid is isolated in valeric acid column 42. Less volatile (heavy) short chain fatty acids are isolated in a similar manner using hexanoic acid column 44, heptanoic acid column 46 and heavy SCFA splitter 48 (for fatty acids having eight or more carbon atoms on the carbon chain). The purification process selected is dependent upon the technology used to isolate short chain carboxylic acids 28 from the fuel components of middle distillate 22.

Individual or mixtures of the short chain carboxylic acids 28 produced in this process can be further processed into short chain carboxylic acid esters by reacting the short chain carboxylic acid with one or more alcohols. Unreacted and/or by-product material is then removed from the product short chain carboxylic acid esters to obtain commercial quality short chain carboxylic acid esters.

In one embodiment of the invention, a triacylglyceride crop oil, biologically generated lipid, animal fat oil or a transesterified derivative of any of these oils (biomass 10) is heated to a temperature ranging from 300° C. to 500° C., in a cracking reactor, at pressures ranging from vacuum conditions to 3000 psia, in the presence of a gaseous environment that can contain an inert gas such as nitrogen, water vapor, hydrogen, a mixture of vapor-phase organic chemicals or any other gaseous substance, for residence times ranging from one to 180 minutes to affect cracking reactions that change the chemical composition of the contents of the cracking reactor. The vapor leaving the cracking reactor (crackate), is subjected to downstream processing that can include cooling and partial condensation, vapor/liquid separation, extraction of by-product chemicals by solvent extraction or other chemical/physical property manipulation, in-situ reaction, distillation or flash separation to produce an acceptable transportation fuel, such as aviation turbine fuel or diesel fuel. The liquid and solids leaving the reactor (residue) are subjected to downstream processing that can include cooling or heating, liquid/solid separation, vapor/liquid separation, vapor/solid separation, extraction of by-product chemicals by solvent extraction or other chemical/physical property manipulation to produce an acceptable fuel by-product or byproducts. Unreacted and partially reacted material 22 separated from either the crackate or the residue may be recycled to the cracking reactor, routed to additional cracking reactors or used in other processes.

Example 1

Short Chain Fatty Acid Production from Soybean Oil

A two liter per hour continuous cracking reactor system was used as the cracking reactor. Thermal cracking under vacuum conditions was applied to soybean oil. Output from the cracking reactor (crackate) was analyzed and then processed further. The light hydrocarbons were removed in a packed distillation column, and the heaviest were removed using a second packed distillation column. This produced a middle distillate liquid containing a high percentage of short chain carboxylic acids. The middle distillate was then mixed with an equal amount of room temperature, purified water and the oil and water phases were then separated. This step removed most of the C2-C4 fatty acids. The oil from this extraction was then mixed with an equal amount of 1M NaOH in purified water and the oil and aqueous phases were then separated. Table 4 summarizes the results of the short chain fatty acid extractions with water and NaOH. The amounts of short chain fatty acids (SCFA) extracted are represented by % (w/w) of middle distillate 18.

TABLE 4

| FA Carbon Chain Length | SCFA in distillate Mean % (w/w) | SD | SCFA extracted with water Mean % (w/w) | SD | SCFA extracted with NaOH Mean % (w/w) | SD |
|---|---|---|---|---|---|---|
| 2  | 2.84 | 0.13  | 2.84 |      | 2.84 |      |
| 3  | 3.23 | 0.19  | 3.23 |      | 3.23 |      |
| 4  | 1.33 | 0.03  | 1.05 | 0.01 | 1.30 |      |
| 5  | 1.64 | 0.03  | 0.51 | 0.03 | 1.49 | 0.01 |
| 6  | 2.14 | 0.05  | 0.05 | 0.06 | 1.88 | 0.04 |
| 7  | 3.06 | 0.06  |      |      | 1.88 | 0.13 |
| 8  | 2.66 | 0.05  |      |      | 0.41 | 0.14 |
| 9  | 2.55 | 0.03  |      |      |      |      |
| 10 | 2.70 | 0.08  |      |      |      |      |
| 11 | 0.31 | 0.01  |      |      |      |      |
| 16 | 0.04 | 0.001 |      |      |      |      |

Example 2

Short Chain Fatty Acid Production from Soybean Oil Using Aqueous Amine

Figure 4:
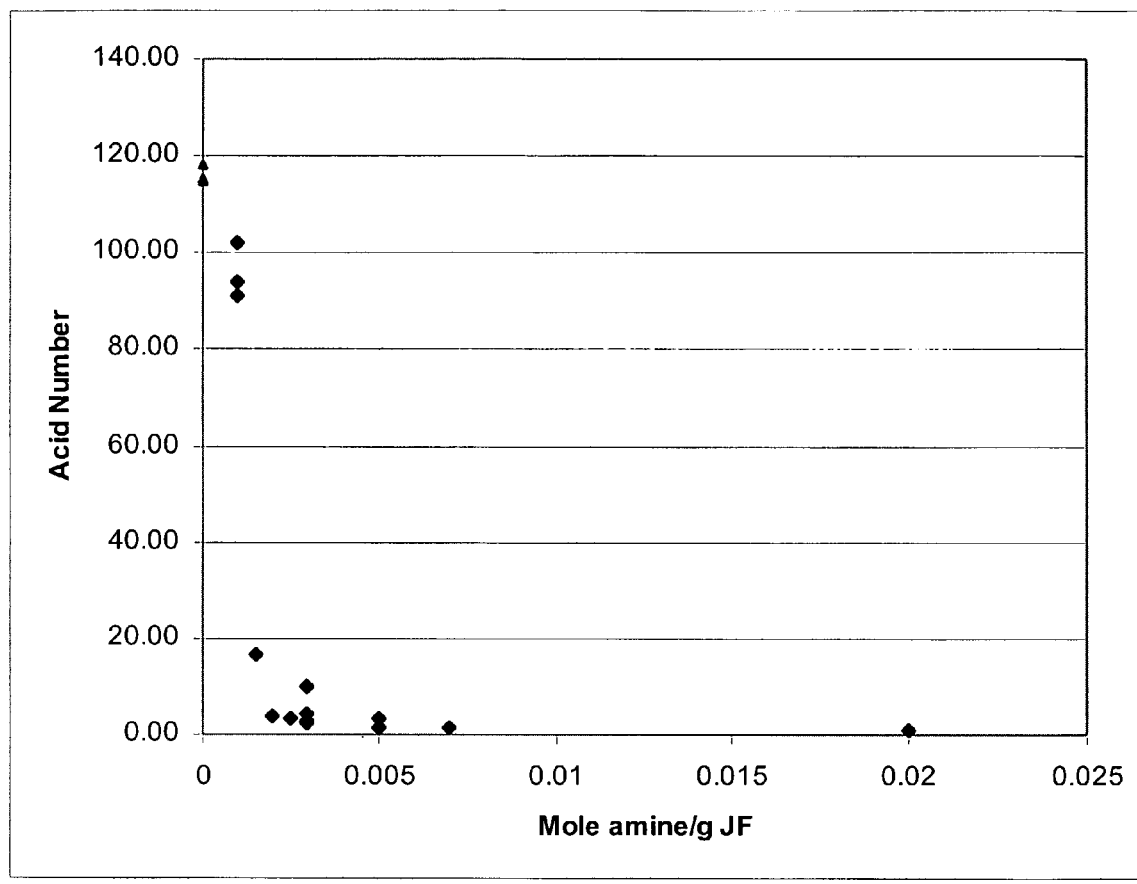
FIG. 4 is a graph illustrating fatty acid extraction with trimethylamine.

As in Example 1, a middle distillate 18 containing a high percentage of short chain carboxylic acids was produced from soybean oil. Middle distillate 18 was then mixed in a separatory funnel with a 25% (w/w) aqueous solution of trimethylamine at room temperature. The amount of aqueous amine solution added was such that 0.002 moles of trimethylamine were present for each gram of middle distillate 18. The aqueous and organic phases were then separated and the acid number of middle distillate 18 was measured according to ASTM method D3242. FIG. 4 illustrates the results of the short chain fatty acid extraction with aqueous amine. As shown, the acid number of middle distillate 18 after extraction falls to near zero, indicating that virtually all of the fatty acids were extracted into the aqueous phase.

Figure 5:
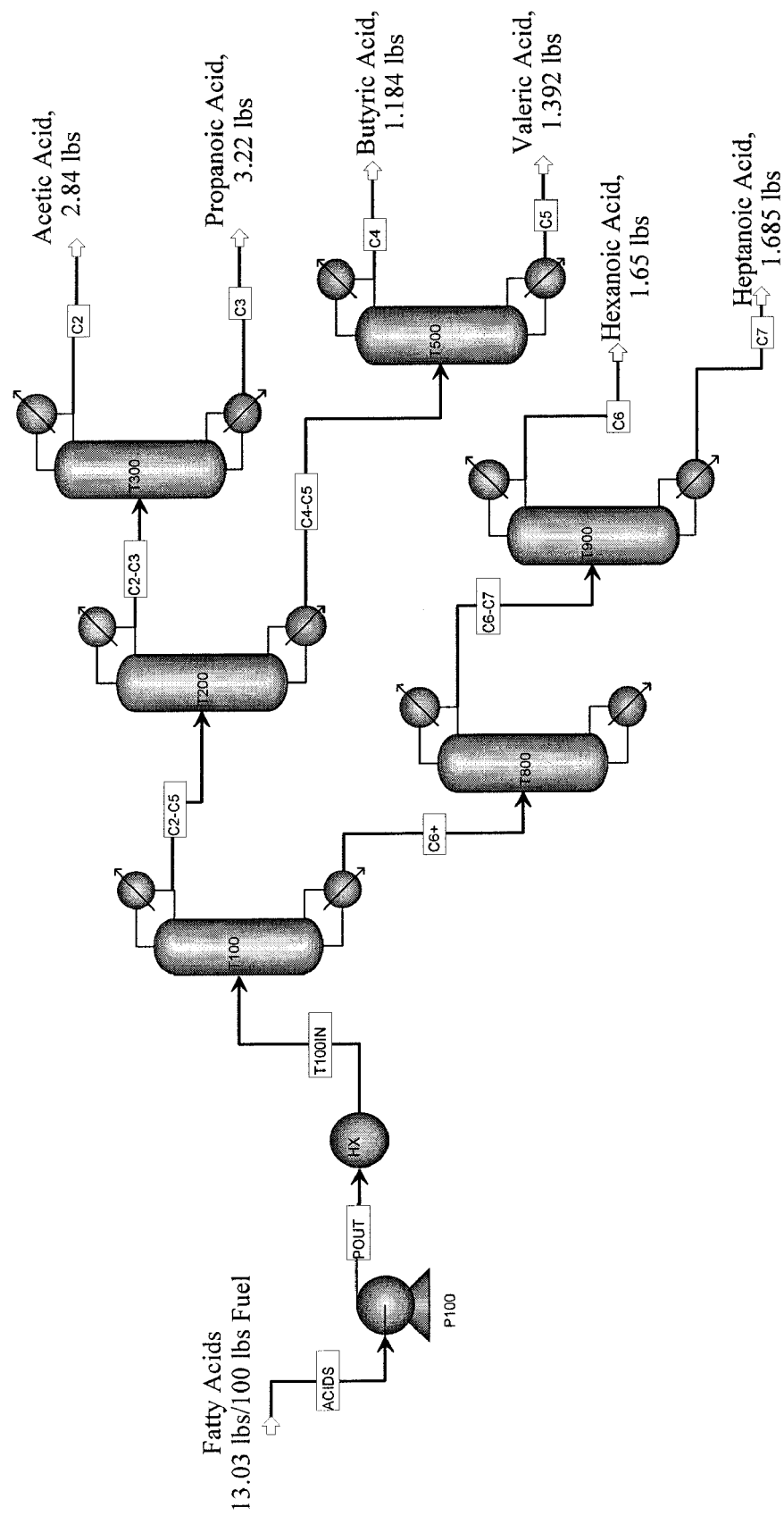
FIG. 5 illustrates an ASPEN Plus simulation model for a series of distillation columns to separate and purify short chain carboxylic acids.

Using the data gathered from these experiments, an ASPEN Plus simulation model was generated for a series of distillation columns to separate and purify the short chain carboxylic acids based on volatility. The simulation results are illustrated in FIG. 5. A mixture of fatty (carboxylic) acids is delivered via pump P100 through heat exchanger HX to distillation column T100. Fatty acids having two to five carbon atoms in the carbon chain are separated from the mixture and sent to distillation column T200. Fatty acids having two or three carbon atoms are separated and sent to distillation column T300. Distillation column T300 separates the two carbon fatty acid (acetic acid) from the three carbon fatty acid (propanoic acid). Likewise, fatty acids having four or five carbon atoms are sent from distillation column T200 to distillation column T500. Distillation column T500 separates the four carbon fatty acid (butyric acid) from the five carbon fatty acid (valeric acid). In a similar fashion, distillation column T800 separates fatty acids having six or seven carbon atoms from those having eight or more. Fatty acids having six or seven carbon atoms are sent to distillation column T900 where the six carbon fatty acid (hexanoic acid) is separated from the seven carbon fatty acid (heptanoic acid). Estimated yields are listed in FIG. 5 for the simulated purification.

The method of producing short chain carboxylic acids and acid esters described herein provides a useful tool for creating valuable chemical compounds from biomass rather than petroleum precursors. The method also allows for the coproduction of chemical compounds useful in fuel applications using the same cracking parameters. Efficiency gains are realized by being able to generate two sets of useful chemical compounds using steps that share some of the same processing conditions.

While the invention has been described with reference to exemplary embodiments, it will be understood by those skilled in the art that various changes may be made and equivalents be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

The invention claimed is:

1. A method for producing a mixture of short chain carboxylic acids from biomass, the method comprising:
   adding a biomass oil containing a compound having a carboxyl group to a reactor vessel;
   heating the biomass oil in the reactor vessel to a temperature ranging from about 390° C. to about 440° C. for a time sufficient to crack the biomass oil;
   removing undesired material, unreacted material, and light ends from the cracked biomass oil; and
   removing a mixture containing at least about 5% of carboxylic acids having carbon chain lengths between C2 and C16.

2. The method of claim 1, wherein the removed mixture contains 20% or more carboxylic acids.

3. The method of claim 2, wherein the removed mixture contains 30% or more carboxylic acids.

4. The method of claim 3, wherein the removed mixture contains 60% or more carboxylic acids.

5. The method of claim 1, further comprising purifying the mixture into one or more carboxylic acids having carbon chain lengths between C2 and C16.

6. The method of claim 5, wherein purification is selected from a group consisting of solvent extraction, distillation and combinations thereof.

7. The method of claim 5, wherein the purified mixture is reacted with an alcohol to produce one or more carboxylic acid esters having carbon chain lengths between C2 and C16.

8. The method of claim 7, wherein the alcohol is selected from a group consisting of methanol, ethanol, normal propanol, iso-propanol, normal butanol, iso-butanol, allyl alcohol and combinations thereof.

9. The method of claim 1, wherein the biomass oil is selected from a group consisting of soybean oil, canola oil, palm oil, sunflower oil, corn oil, flaxseed oil, jatropha oil, cottonseed oil, safflower oil, crambe oil, evening primrose oil, sesame oil, rapeseed oil, olive oil, coconut oil, camelina, jojoba, pennycress, tomato and combinations thereof.

10. The method of claim 1, wherein the biomass oil is heated in the reactor vessel for a time ranging from one minute to 180 minutes.

11. The method of claim 1, wherein the heating in the reactor vessel occurs in a gaseous environment, wherein the gaseous environment includes at least one of an inert gas, nitrogen, water vapor, hydrogen, or a mixture of vapor-phase organic chemicals.

12. The method of claim 1, wherein the reactor vessel is of a type selected from a group consisting of batch, continuous flow through, flow through packed bed, and fluidized bed.

13. The method of claim 1, wherein the mixture includes alkanes, alkenes, aromatics, cycloparaffins, or alcohols having carbon chain lengths between C4 and C12 and fatty carboxylic acids having carbon chain lengths between C2 and C16.

14. The method of claim 13, wherein the mixture includes alkanes, alkenes, aromatics, cycloparaffins, or alcohols having carbon chain lengths between C4 and C8 and fatty carboxylic acids having carbon chain lengths between C2 and C10.

15. The method of claim 6, wherein solvent extraction comprises:
   contacting the mixture with a solvent selected from a group consisting of water, a basic aqueous solution, or an aqueous amine solution;
   removing the one or more carboxylic acids and the solvent from the mixture; and
   separating the one or more carboxylic acids from the solvent.

16. The method of claim 15, wherein the carboxylic acids are recovered from the solvent by distillation, evaporation, pervaporation, pH adjustment, or other physical or chemical separation principle.

17. A method for producing short chain carboxylic acids and a fuel composition having a low cloud point from a biomass oil containing a compound having a carboxyl group, the method comprising:
   adding the biomass oil to a reactor vessel;
   heating the biomass oil in the reactor vessel to a temperature ranging from about 390° C. to about 440° C. at a pressure ranging from about vacuum conditions to about 3000 psia for a time sufficient to crack the biomass oil;
   removing undesired material, unreacted material, and light ends from the cracked biomass oil;
   collecting fractions of the cracked biomass oil including at least one of C4 to C16 alkanes, alkenes, aromatics, cycloparaffins, or alcohols; C2 to C16 fatty acids; or C2 to C16 fatty acid methyl esters;
   removing a mixture containing carboxylic acids having carbon chain lengths between C2 and C16; and
   combining collected fractions of cracked biomass oil to produce a fuel composition having a cloud point less than −10° C.

18. The method of claim 1, wherein the carboxylic acids in the mixture are saturated carboxylic acids.

19. The method of claim 18, wherein the mixture contains saturated carboxylic acids selected from the group consisting of acetic acid, propanoic acid, butyric acid, valeric acid, hexanoic acid, heptanoic acid and combinations thereof.

20. The method of claim 1, wherein the biomass oil comprises a triacylglyceride.

21. The method of claim 1, wherein the biomass oil is soybean oil.

22. The method of claim 1, wherein the biomass oil is heated in the reactor vessel at a pressure ranging from about vacuum conditions to about 3000 psia.

* * * * *

UNITED STATES PATENT AND TRADEMARK OFFICE
CERTIFICATE OF CORRECTION

PATENT NO. : 8,076,504 B2
APPLICATION NO. : 12/319028
DATED : December 13, 2011
INVENTOR(S) : Alena Kubatova et al.

It is certified that error appears in the above-identified patent and that said Letters Patent is hereby corrected as shown below:

In the Claims

Col. 16, Line 9
 Delete "fatty"

Col. 16, Line 14
 Delete "fatty"

Signed and Sealed this
Twenty-sixth Day of November, 2013

Margaret A. Focarino
*Commissioner for Patents of the United States Patent and Trademark Office*